(12) United States Patent
Hagfors et al.

(10) Patent No.: US 12,064,252 B2
(45) Date of Patent: Aug. 20, 2024

(54) SYSTEM AND METHOD FOR CARDIAC MAPPING

(71) Applicant: ST. JUDE MEDICAL, CARDIOLOGY DIVISION, INC., St. Paul, MN (US)

(72) Inventors: Mark Hagfors, North Oaks, MN (US); Travis Dahlen, Forest Lake, MN (US); Daniel R Starks, Lake Elmo, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 69 days.

(21) Appl. No.: 17/604,281

(22) PCT Filed: Apr. 3, 2020

(86) PCT No.: PCT/US2020/026675
§ 371 (c)(1),
(2) Date: Oct. 15, 2021

(87) PCT Pub. No.: WO2020/214439
PCT Pub. Date: Oct. 22, 2020

(65) Prior Publication Data
US 2022/0192577 A1  Jun. 23, 2022

Related U.S. Application Data

(60) Provisional application No. 62/835,937, filed on Apr. 18, 2019.

(51) Int. Cl.
*A61B 5/367* (2021.01)
*A61B 5/318* (2021.01)
*A61B 5/343* (2021.01)

(52) U.S. Cl.
CPC .............. *A61B 5/367* (2021.01); *A61B 5/318* (2021.01); *A61B 5/343* (2021.01)

(58) Field of Classification Search
CPC ................................ A61B 5/367; A61B 5/343
See application file for complete search history.

(56) References Cited

U.S. PATENT DOCUMENTS

| 5,697,377 A | 12/1997 | Wittkampf |
| 5,983,126 A | 11/1999 | Wittkampf |

(Continued)

FOREIGN PATENT DOCUMENTS

| CN | 107087290 A | 8/2017 | |
| WO | WO2016/061384 | * 4/2016 | ............. A61B 5/042 |

OTHER PUBLICATIONS

C.D. Cantwell et al: "Techniques for automated local activation time annotation and conduction velocity estimation in cardiac mapping", Computers in Biology and Medicine., vol. 65, Oct. 1, 2015 (Oct. 1, 2015), pp. 229-242.

(Continued)

*Primary Examiner* — Catherine M Voorhees
*Assistant Examiner* — Roland Dinga
(74) *Attorney, Agent, or Firm* — Wiley Rein LLP (57) ABSTRACT

An electroanatomical mapping system can map electrical activation of tissue, and in particular create a slow conduction map, using a plurality of electrophysiology data points, each including local activation timing information, by computing a slow conduction metric for each point using the local activation timing information. The slow conduction metric can be used to classify points as no conduction points, slow conduction points, and normal conduction points, and the results can be graphically expressed, including as an animated representation of an activation wavefront propagating along a three-dimensional anatomical surface model.

17 Claims, 9 Drawing Sheets

(56) References Cited

U.S. PATENT DOCUMENTS

| | | |
|---|---|---|
| 6,640,119 B1 | 10/2003 | Budd et al. |
| 6,728,562 B1 | 4/2004 | Budd et al. |
| 6,939,309 B1 | 9/2005 | Beatty et al. |
| 6,947,785 B1 | 9/2005 | Beatty et al. |
| 6,978,168 B2 | 12/2005 | Beatty et al. |
| 6,990,370 B1 | 1/2006 | Beatty et al. |
| 7,263,397 B2 | 8/2007 | Hauck et al. |
| 7,885,707 B2 | 2/2011 | Hauck |
| 8,909,502 B2 | 12/2014 | Voth |
| 9,364,160 B2 | 6/2016 | Marziliano et al. |
| 9,474,491 B2 | 10/2016 | Li et al. |
| 10,136,829 B2 | 11/2018 | Deno et al. |
| 10,296,810 B2 | 5/2019 | Lee et al. |
| 10,441,187 B2 | 10/2019 | Afonso et al. |
| 2010/0162786 A1 | 7/2010 | Keenan et al. |
| 2015/0057507 A1* | 2/2015 | Koyrakh .............. A61B 5/7246 600/301 |
| 2015/0196215 A1 | 7/2015 | Laughner et al. |
| 2017/0360319 A1 | 12/2017 | Bertram |

OTHER PUBLICATIONS

Nakasuka Kosuke et al: ""Window Sliding" analysis combined with high-density and rapid electroanatomical mapping: its efficacy and the outcome of catheter ablation of atrial tachycardia", Heart and Vessels, Springer, Berlin, DE, vol. 32, No. 8, Mar. 8, 2017 (Mar. 8, 2017), pp. 984-996.

Samuel O Oduneye et al: "The Feasibility of Endocardial Propagation Mapping Using Magnetic Resonance Guidance in a Swine Model, and Comparison With Standard Electroanatomic Mapping", IEEE Transactions on Medical Imaging, IEEE Service Center, Piscataway, NJ, US, vol. 31, No. 4, Apr. 1, 2012 (Apr. 1, 2012), pp. 977-983.

Alcaine Alejandro et al: "Spatiotemporal model-based estimation of high-density atrial fibrillation activation maps", Digital Signal Processing, Academic Press, Orlando, FL, US, vol. 54, Apr. 9, 2016 (Apr. 9, 2016), pp. 64-74.

* cited by examiner

SYSTEM AND METHOD FOR CARDIAC MAPPING

CROSS-REFERENCE TO RELATED APPLICATIONS

This application claims the benefit of U.S. provisional application No. 62/835,937, filed 18 Apr. 2019, which is hereby incorporated by reference as though fully set forth herein.

BACKGROUND

The present disclosure relates generally to cardiac mapping, such as may be performed in cardiac diagnostic and therapeutic procedures. In particular, the present disclosure relates to systems, apparatuses, and methods for generating electrophysiology maps from data collected by a roving electrophysiology probe, such as a high density ("HD") grid catheter or other multi-electrode device. Even more particularly, the electrophysiology maps disclosed herein facilitate the identification of regions of slow conduction and/or block using local activation timing information.

Anatomical mapping, such as cardiac electrophysiological mapping, is used in numerous diagnostic and therapeutic procedures. In certain procedures, for example, various components associated with a depolarization wave are detected from electrogram signals obtained from a diagnostic catheter, and are used to generate a map, such as a local activation time ("LAT") map. Typically, such maps are static maps that, when drawn, employ colors and/or shading to represent parameters, such as activation time.

In some cases, it may be desirable to understand the propagation of a cardiac activation wavefront. In particular, when studying cardiac arrhythmia, a practitioner may wish to identify areas of slow conduction and/or block (e.g., no conduction).

BRIEF SUMMARY

Disclosed herein is a method of mapping electrical activation of tissue, including: receiving, at an electroanatomical mapping system, a plurality of electrophysiology data points, each of the plurality of electrophysiology data points including local activation timing information; and for each of the plurality of electrophysiology data points, the electroanatomical mapping system computing a slow conduction metric from the local activation timing information, thereby creating a slow conduction map.

The method can also include: the electroanatomical mapping system classifying a first subset of the plurality of electrophysiology data points as no conduction electrophysiology data points; and the electroanatomical mapping system classifying a second subset of the plurality of electrophysiology data points as slow conduction electrophysiology data points.

In additional embodiments of the disclosure, the method can include the electroanatomical mapping system outputting a graphical representation of the slow conduction map on a three-dimensional anatomical surface model. For instance, the electroanatomical mapping system can graphically represent regions of no conduction on the three-dimensional anatomical surface model using a first display convention and can represent regions of slow conduction on the three-dimensional anatomical surface model using a second display convention.

Alternatively, the graphical representation of the slow conduction map can include an animated representation of an activation wavefront propagating along the three-dimensional anatomical surface model. For example, the electroanatomical mapping system can generate the animated representation of the activation wavefront propagating along the three-dimensional anatomical surface model by executing steps including: generating a series of frames, wherein each frame of the series of frames corresponds to an image of the slow conduction map at a point in time and includes a static representation of the activation wavefront at the point in time, wherein a visibility of the static representation of the activation wavefront at the point in time is related to the slow conduction metric at a position of the activation wavefront at the point in time; and displaying the series of frames in chronological sequence. In connection with such animated representations, it is contemplated that the visibility of the static representation of the activation wavefront can be directly related to the slow conduction metric at the position of the activation wavefront at the point in time.

According to aspects of the disclosure, the electroanatomical mapping system can compute the slow conduction metric using a weighted standard deviation of the local activation timing information. Alternatively, the electroanatomical mapping system can compute the slow conduction metric using a weighted variance of the local activation timing information.

Also disclosed herein is a method of mapping electrical activation of tissue, including the following steps: receiving a local activation time map comprising a plurality of electrophysiology data points, each electrophysiology data point including local activation timing information; and for each electrophysiology data point of the plurality of electrophysiology data points, computing a slow conduction metric using the local activation timing information for a subset of the plurality of electrophysiology data points within a preset distance of the respective electrophysiology data point, thereby creating a slow conduction map.

The slow conduction metric can be computed using one of a weighted variance of the local activation timing information for the subset of the plurality of electrophysiology data points and a weighted standard deviation of the local activation timing information for the subset of the plurality of electrophysiology data points. The weighting can, for example, be inversely related to distance from the respective electrophysiology data point (e.g., as distance from the respective electrophysiology data point increases, the weight decreases).

The method can also include outputting a graphical representation of the slow conduction map on a three-dimensional anatomical surface model. In embodiments of the disclosure, the graphical representation of the slow conduction map includes a graphical representation of at least one region of no conduction represented on the three-dimensional anatomical surface model using a first display convention; and a graphical representation of at least one region of slow conduction represented on the three-dimensional anatomical surface model using a second display convention.

In other embodiments of the disclosure, the graphical representation of the slow conduction map includes an animated representation of a cardiac activation wavefront. The animated representation of the cardiac activation wavefront can include a plurality of frames, wherein each frame corresponds to a playback time and includes a static representation of the cardiac activation wavefront at the playback time, and wherein a visibility of the static representation of the cardiac activation wavefront is related to the slow conduction metric at a position of the cardiac activation wavefront at the playback time. It is contemplated that the visibility of the static representation of the cardiac activation wavefront can be directly related to the slow conduction metric at the position of the cardiac activation wavefront at the playback time.

The instant disclosure also provides an electroanatomical mapping system for generating a map of electrical activation of tissue. The system includes an activation mapping processor configured to: receive a local activation time map comprising a plurality of electrophysiology data points, each electrophysiology data point including local activation timing information; and for each electrophysiology data point of the plurality of electrophysiology data points, compute a slow conduction metric using the local activation timing information for a subset of the plurality of electrophysiology data points within a preset distance of the respective electrophysiology data point, thereby creating a slow conduction map. The system optionally further includes a mapping processor configured to output a graphical representation of the slow conduction map, such as an animated representation of a cardiac activation wavefront.

The foregoing and other aspects, features, details, utilities, and advantages of the present invention will be apparent from reading the following description and claims, and from reviewing the accompanying drawings.

While multiple embodiments are disclosed, still other embodiments of the present disclosure will become apparent to those skilled in the art from the following detailed description, which shows and describes illustrative embodiments. Accordingly, the drawings and detailed description are to be regarded as illustrative in nature and not restrictive.

DETAILED DESCRIPTION

The instant disclosure provides systems, apparatuses, and methods for generating electrophysiology maps, and more particularly maps of electrical activation of tissue, that facilitate the identification of regions of slow conduction and/or block. For purposes of illustration, aspects of the disclosure will be described with reference to cardiac electrophysiology procedures conducted using a high density (HD) grid catheter, such as the Advisor™ HD grid mapping catheter from Abbott Laboratories (Abbott Park, Illinois), in conjunction with an electroanatomical mapping system, such as the EnSite Precision™ cardiac mapping system, also from Abbott Laboratories. Those of ordinary skill in the art will understand, however, how to apply the teachings herein to good advantage in other contexts and/or with respect to other devices.

Figure 1:
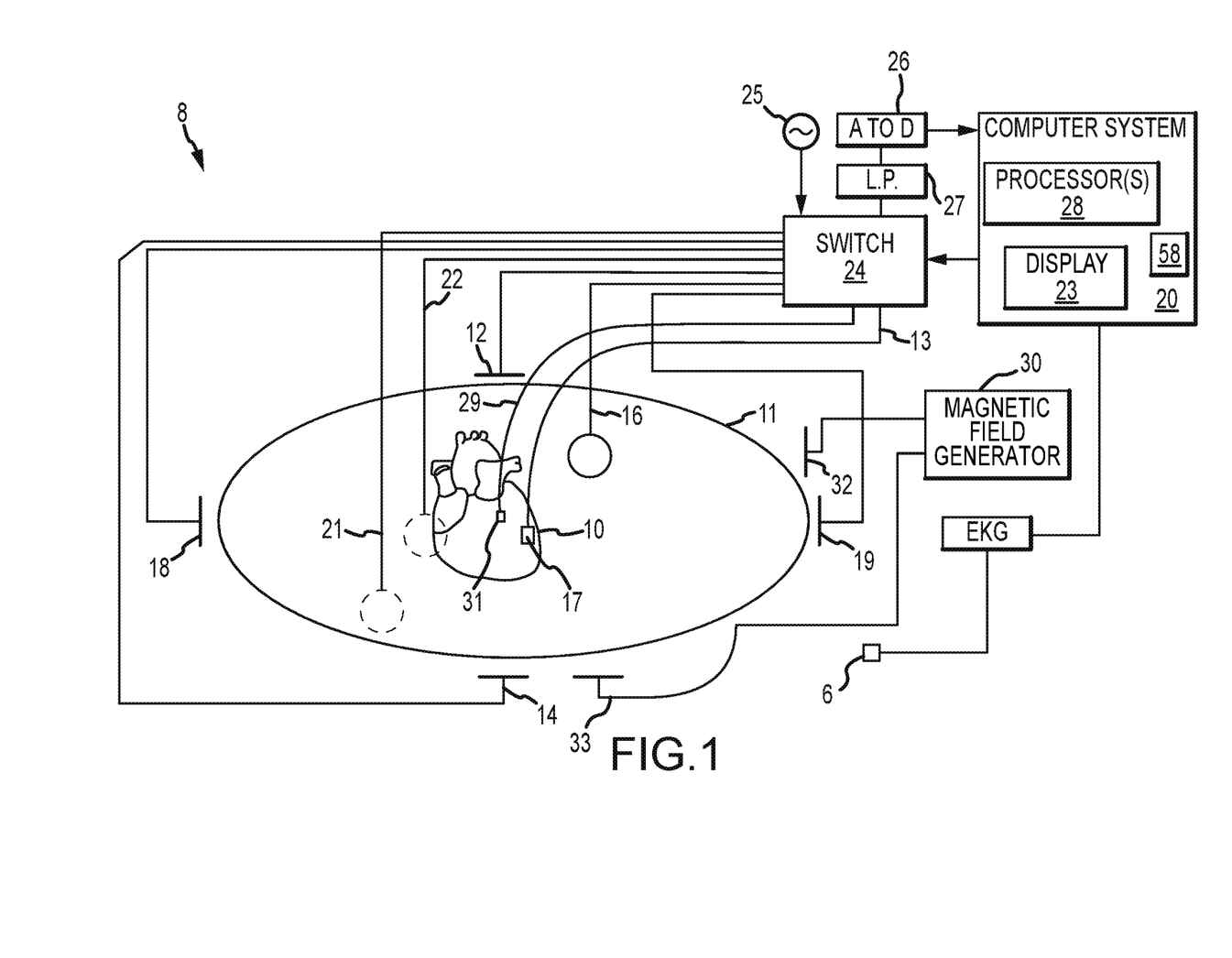
FIG. 1 is a schematic diagram of an exemplary electroanatomical mapping system.

FIG. 1 shows a schematic diagram of an exemplary electroanatomical mapping system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data at a plurality of points along a cardiac surface and store the measured data in association with location information for each measurement point at which the electrophysiology data was measured, for example to create a diagnostic data map of the patient's heart 10.

As one of ordinary skill in the art will recognize, system 8 determines the location, and in some aspects the orientation, of objects, typically within a three-dimensional space, and expresses those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only a single lead 6 and its connection to computer 20 is illustrated in FIG. 1.

A representative catheter 13 having at least one electrode 17 is also shown. This representative catheter electrode 17 is referred to as the "roving electrode," "moving electrode," or "measurement electrode" throughout the specification. Typically, multiple electrodes 17 on catheter 13, or on multiple such catheters, will be used. In one embodiment, for example, the system 8 may comprise sixty-four electrodes on twelve catheters disposed within the heart and/or vasculature of the patient. In other embodiments, system 8 may utilize a single catheter that includes multiple (e.g., eight) splines, each of which in turn includes multiple (e.g., eight) electrodes.

Figure 2:
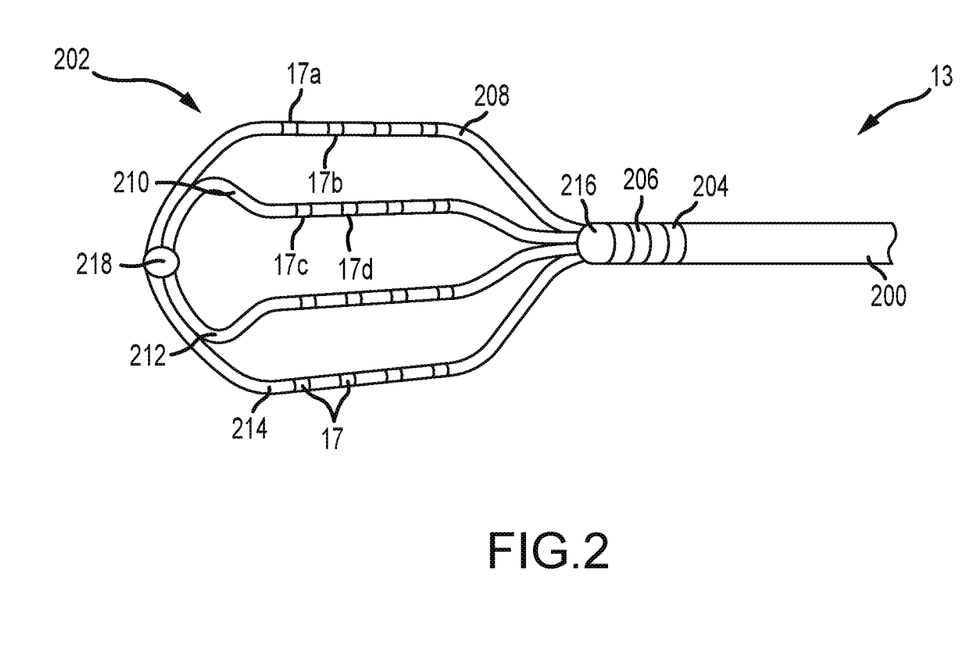
FIG. 2 depicts an exemplary catheter that can be used in connection with aspects of the instant disclosure.

The foregoing embodiments are merely exemplary, however, and any number of electrodes and/or catheters may be used. For example, for purposes of this disclosure, a segment of an exemplary multi-electrode catheter, and in particular an HD grid catheter, is shown in FIG. 2. HD grid catheter 13 includes a catheter body 200 coupled to a paddle 202. Catheter body 200 can further include first and second body electrodes 204, 206, respectively. Paddle 202 can include a first spline 208, a second spline 210, a third spline 212, and a fourth spline 214, which are coupled to catheter body 200 by a proximal coupler 216 and to each other by a distal coupler 218. In one embodiment, first spline 208 and fourth spline 214 can be one continuous segment and second spline 210 and third spline 212 can be another continuous segment. In other embodiments, the various splines 208, 210, 212, 214 can be separate segments coupled to each other (e.g., by proximal and distal couplers 216, 218, respectively). It should be understood that HD catheter 13 can include any number of splines; the four-spline arrangement shown in FIG. 2 is merely exemplary.

As described above, splines 208, 210, 212, 214 can include any number of electrodes 17; in FIG. 2, sixteen electrodes 17 are shown arranged in a four-by-four array. It should also be understood that electrodes 17 can be evenly and/or unevenly spaced, as measured both along and between splines 208, 210, 212, 214.

Catheter 13 (or multiple such catheters) are typically introduced into the heart and/or vasculature of the patient via one or more introducers and using familiar procedures. Indeed, various approaches to introduce catheter 13 into a patient's heart, such as transseptal approaches, will be familiar to those of ordinary skill in the art, and therefore need not be further described herein.

Since each electrode 17 lies within the patient, location data may be collected simultaneously for each electrode 17 by system 8. Similarly, each electrode 17 can be used to gather electrophysiological data from the cardiac surface (e.g., surface electrograms). The ordinarily skilled artisan will be familiar with various modalities for the acquisition and processing of electrophysiology data points (including, for example, both contact and non-contact electrophysiological mapping), such that further discussion thereof is not necessary to the understanding of the techniques disclosed herein. Likewise, various techniques familiar in the art can be used to generate a graphical representation of a cardiac geometry and/or of cardiac electrical activity from the plurality of electrophysiology data points. Moreover, insofar as the ordinarily skilled artisan will appreciate how to create electrophysiology maps from electrophysiology data points, the aspects thereof will only be described herein to the extent necessary to understand the present disclosure.

Returning now to FIG. 1, in some embodiments, an optional fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20 may comprise, for example, a conventional general-purpose computer, a special-purpose computer, a distributed computer, or any other type of computer. The computer 20 may comprise one or more processors 28, such as a single central processing unit ("CPU"), or a plurality of processing units, commonly referred to as a parallel processing environment, which may execute instructions to practice the various aspects described herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any number of electrodes) could be positioned in any other effective arrangement for driving a current to or sensing a current from an electrode in the heart. For example, multiple electrodes could be placed on the back, sides, and/or belly of patient 11. Additionally, such non-orthogonal methodologies add to the flexibility of the system. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17 placed in the heart 10 are exposed to the field from a current pulse and are measured with respect to ground, such as belly patch 21. In practice the catheters within the heart 10 may contain more or fewer electrodes than the sixteen shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which system 8 measures positions. Data sets from each of the surface electrodes, the internal electrodes, and the virtual electrodes may all be used to determine the location of the roving electrodes 17 within heart 10.

The measured voltages may be used by system 8 to determine the location in three-dimensional space of the electrodes inside the heart, such as roving electrodes 17 relative to a reference location, such as reference electrode 31. That is, the voltages measured at reference electrode 31 may be used to define the origin of a coordinate system, while the voltages measured at roving electrodes 17 may be used to express the location of roving electrodes 17 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described, for example, in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

Therefore, in one representative embodiment, system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In aspects of the disclosure, system 8 can be a hybrid system that incorporates both impedance-based (e.g., as described above) and magnetic-based localization capabilities. Thus, for example, system 8 can also include a magnetic source 30, which is coupled to one or more magnetic field generators. In the interest of clarity, only two magnetic field generators 32 and 33 are depicted in FIG. 1, but it should be understood that additional magnetic field generators (e.g., a total of six magnetic field generators, defining three generally orthogonal axes analogous to those defined by patch electrodes 12, 14, 16, 18, 19, and 22) can be used without departing from the scope of the present teachings. Likewise, those of ordinary skill in the art will appreciate that, for purposes of localizing catheter 13 within the magnetic fields so generated, can include one or more magnetic localization sensors (e.g., coils).

In some embodiments, system 8 is the EnSite™ Velocity™ or EnSite Precision™ cardiac mapping and visualization system of Abbott Laboratories. Other localization systems, however, may be used in connection with the present teachings, including for example the RHYTHMIA HDX™ mapping system of Boston Scientific Corporation (Marlborough, Massachusetts), the CARTO navigation and location system of Biosense Webster, Inc. (Irvine, California), the AURORA® system of Northern Digital Inc. (Waterloo, Ontario), Sterotaxis, Inc.'s NIOBE® Magnetic Navigation System (St. Louis, Missouri), as well as MediGuide™ Technology from Abbott Laboratories.

The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

Aspects of the disclosure relate to electrophysiological mapping, and in particular to mapping electrical activation of tissue in order to facilitate the identification of regions of slow conduction and/or block. Graphical representations of such maps can also be output, for example on display 23. System 8 can therefore include an activation mapping module 58 that can be used to generate an anatomical map, and which may incorporate a display module to allow for graphical output thereof (e.g., to display 23).

Figure 3:
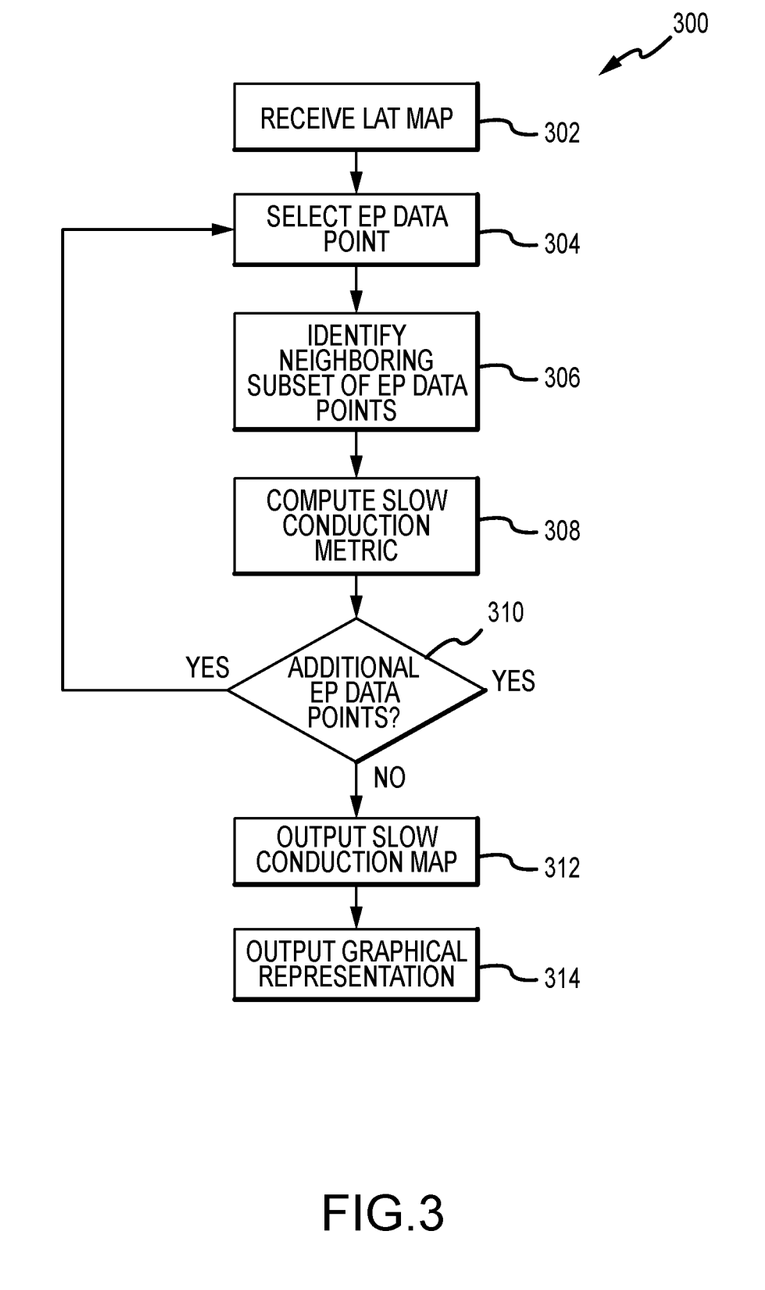
FIG. 3 is a flowchart of representative steps that can be carried out according to exemplary embodiments disclosed herein.

One exemplary method according to the present teachings will be explained with reference to the flowchart 300 of representative steps presented as FIG. 3. In some embodiments, for example, flowchart 300 may represent several exemplary steps that can be carried out by electroanatomical mapping system 8 of FIG. 1 (e.g., by processor 28 and/or activation mapping module 58). It should be understood that the representative steps described below can be either hardware- or software-implemented. For the sake of explanation, the term "signal processor" is used herein to describe both hardware- and software-based implementations of the teachings herein.

In block 302, system 8 receives a local activation time (LAT) map. As those of ordinary skill in the art will appreciate, a LAT map is an electrophysiology map, and therefore includes a plurality of electrophysiology data points, each of which in turn is associated with (at least) local activation timing information.

Blocks 304-310 are exemplary steps that system 8 may carry out to compute a slow conduction metric for a given electrophysiology data point within the LAT map received in block 302. In block 304, system 8 selects an electrophysiology data point (the "selected electrophysiology data point"), while, in block 306, system 8 identifies a subset of the electrophysiology data points (the "neighboring subset") that fall within a preset distance (e.g., a radius of about 2 mm) of the selected electrophysiology data point.

In block 308, system 8 uses the local activation timing for the neighboring subset to compute a slow conduction metric for the selected EP data point. In embodiments of the disclosure, the slow conduction metric is computed as a weighted standard deviation (or weighted variance) of the local activation times for the neighboring subset.

The weight given to the local activation time for any member of the neighboring subset is inversely related to the distance therefrom to the selected EP data point. In other words, lower weights are assigned to members of the neighboring subset that are further away from the selected EP data point, while higher weights are assigned to members of the neighboring subset that are closer to the selected EP data point. In embodiments of the disclosure, the weight falls of linearly with distance from the selected EP data point, though other weighting schemes or functions are likewise within the scope of the instant disclosure.

Decision block 310 considers whether there are additional electrophysiology data points for which a slow conduction metric should be computed. If so (the "YES" exit from block 310), then the process repeats from block 304 with a new selected electrophysiology data point. If not (the "NO" exit from block 310), then system 8 outputs a slow conduction map in block 312.

In block 314, system 8 can output a graphical representation of the slow conduction map, for example on a three-dimensional anatomical surface model, in order to aid a practitioner in identifying regions of no and/or slow conduction. Various graphical representations are contemplated within the scope of the present teachings. Insofar as those of ordinary skill in the art will be generally familiar with the graphical representations of electrophysiology maps, however, details of the graphical representations of the slow conduction maps disclosed herein will be limited to those necessary to the understanding of the instant disclosure.

Figure 4:
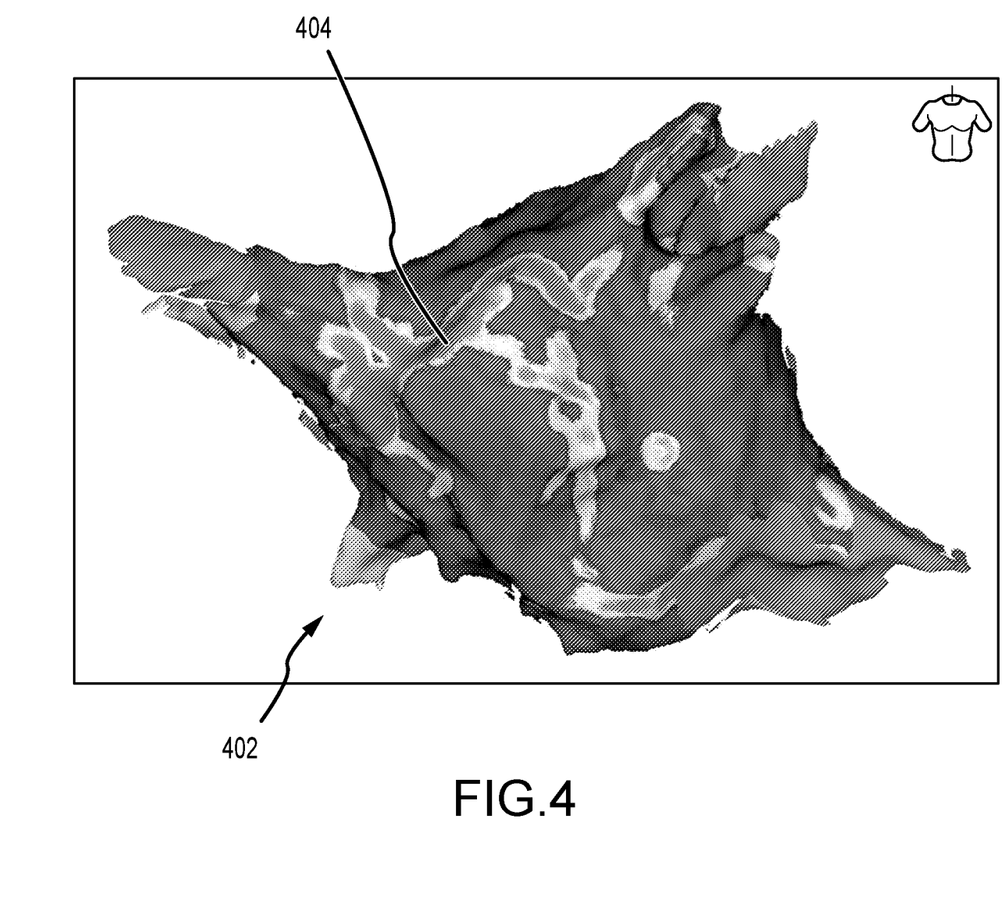
FIG. 4 is a representative graphical representation of a slow conduction map according to aspects of the instant disclosure.

For instance, in some aspects of the disclosure, system 8 outputs the graphical representation of the slow conduction map using a standard mapping convention, such as a color spectrum, a grayscale, a pattern density range, or the like. In this regard, FIG. 4 depicts a graphical representation 402 of a slow conduction map in grayscale. Potential lines of slow conduction and/or no conduction 404 are visible. Advantageously, the use of weighted values when computing the slow conduction metric contribute to smoothness in graphical representation 402.

In additional aspects of the disclosure, system 8 can classify electrophysiology data points, based on their respective slow conduction metrics, as either no conduction electrophysiology data points, slow conduction electrophysiology data points, or normal conduction electrophysiology data points. It is contemplated that a practitioner can select the threshold or cutoff values for each classification of data points. For purposes of illustration, however, for a linearly-weighted radius of about 2 mm (as described above), no conduction electrophysiology data points can have a slow conduction metric of less than about 0.4 ms, while slow conduction electrophysiology data points can have a slow conduction metric between about 0.4 ms and about 1.0 ms.

Once system 8 has classified the electrophysiology data points, it can graphically represent regions of no conduction (e.g., containing the no conduction electrophysiology data points) using a first display convention (e.g., a single color) and regions of slow conduction (e.g., containing the slow conduction electrophysiology data points) using a second display convention (e.g., a single color pattern). Regions of normal conduction (e.g., containing the normal conduction electrophysiology data points) can be displayed using a color scale.

Figure 5:
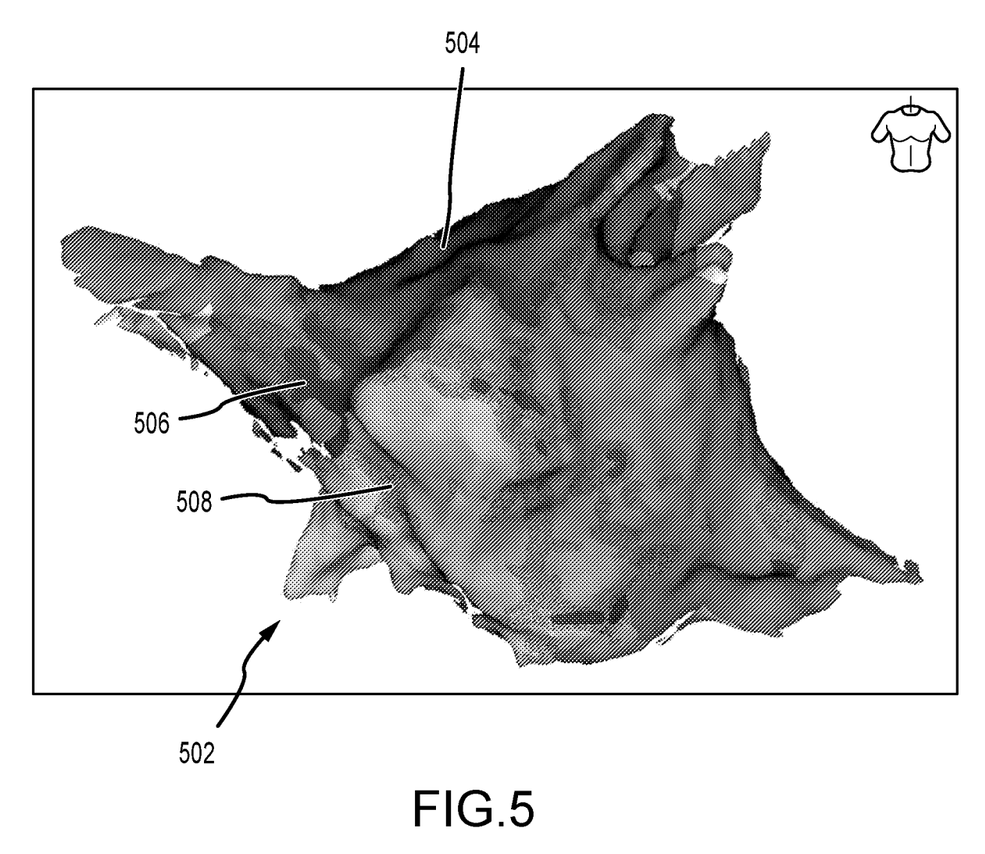
FIG. 5 is a representative graphical representation of a slow conduction map according to another embodiment of the instant disclosure.

FIG. 5 depicts a corresponding graphical representation 502, where regions of normal conduction 504 are depicted using a traditional color scale. Regions of no conduction, however, are depicted using a single, solid color (e.g., brown) 506, while regions of slow conduction are depicted using the same, single color (e.g., brown) with stippling 508.

In still other embodiments of the disclosure, system 8 outputs an animated representation of the slow conduction map by depicting an activation wavefront as it propagates along the three-dimensional anatomical model. Those of ordinary skill in the art will be generally familiar with animated representations of propagating activation wavefronts.

For example, United States patent application publication no. 2017/0360319, which is hereby incorporated by reference as though fully set forth herein, describes the use of static frames, each of which is specific to a particular point in time and includes a timing marker representing the position of the activation wavefront at that point in time. The visibility (e.g., opacity and/or brightness) of any given timing marker in any given frame can be related to the distance from that marker to the position of the activation wavefront at the corresponding point in time, such that a timing marker increases in visibility over a series of frames preceding the arrival of the activation wavefront, reaches its maximum visibility in frames where it coincides with the position of the activation wavefront, and decrease in visibility over a series of frames after the activation wavefront passes. Thus, when the frames are displayed in chronological sequence, the timing marker fades in, reaches a maximum visibility, and then fades out, such that the activation wavefront appears to move across the surface of the three-dimensional anatomical model in a manner similar to that of objects contained in a motion picture.

Typically, however, animated representations of electrical activation wavefronts emphasize areas of fast conduction. Aspects of the instant disclosure, on the other hand, emphasize areas of slow conduction and/or no conduction.

In particular, the rate at which the visibility of the graphical representation of the activation wavefront decays after the activation wavefront passes by a given location is related to the slow conduction metric at that location. Higher slow conduction metrics at a given location will result in longer decay times (e.g., the graphical representation of the activation wavefront at that location remains visible longer), while lower slow conduction metrics at a given location will result in shorter decay times (e.g., the graphical representation of the activation wavefront at the location disappears faster). This gives the visual impression of the activation wavefront slowing down within regions of slow conduction and/or no conduction.

Figure 6:
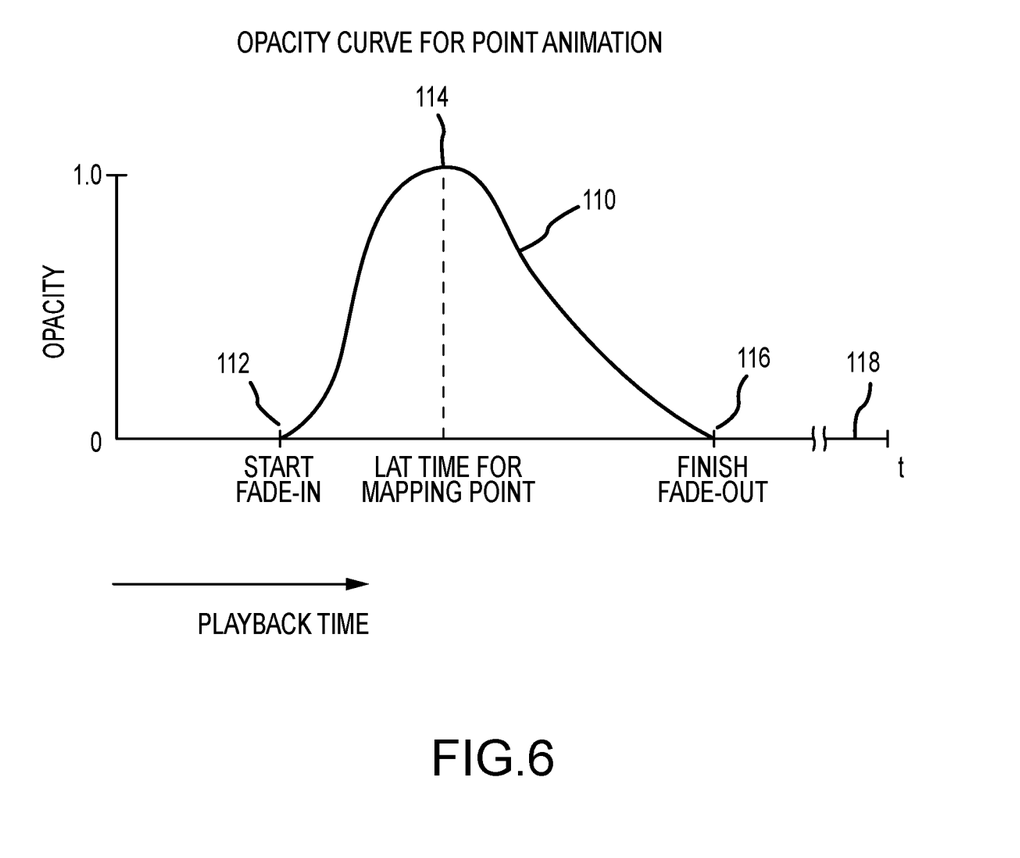
FIG. 6 is an illustrative curve showing the change in opacity (that is, visibility) of a graphical representation of a particular location on a cardiac surface over time as an activation wavefront approaches and passes through that location.

FIG. 6 is a representative curve for the visibility of the graphical representation of the activation wavefront at any particular location. At time 112, the graphical representation begins to fade in as the activation wavefront approaches the particular location, reaching its maximum visibility at time 114, which is the time at which the activation wavefront coincides with the particular location. It then fades out as it moves away from the particular location, until disappearing completely at time 116. The length of decay slope 110 along the horizontal axis (e.g., between time 114 of maximum visibility and time 116 at which fade out is completed) is directly related to the slow conduction metric at the particular location—the higher the slow conduction metric, the wider decay slope 110 will be.

In embodiments of the disclosure, decay slope 110 can be a non-linear function of the slow conduction metric that varies in the range of about 2% to about 52% of the cycle length of the rhythm, with a higher slow conduction metric corresponding with a longer duration decay slope 110.

Figure 7A:
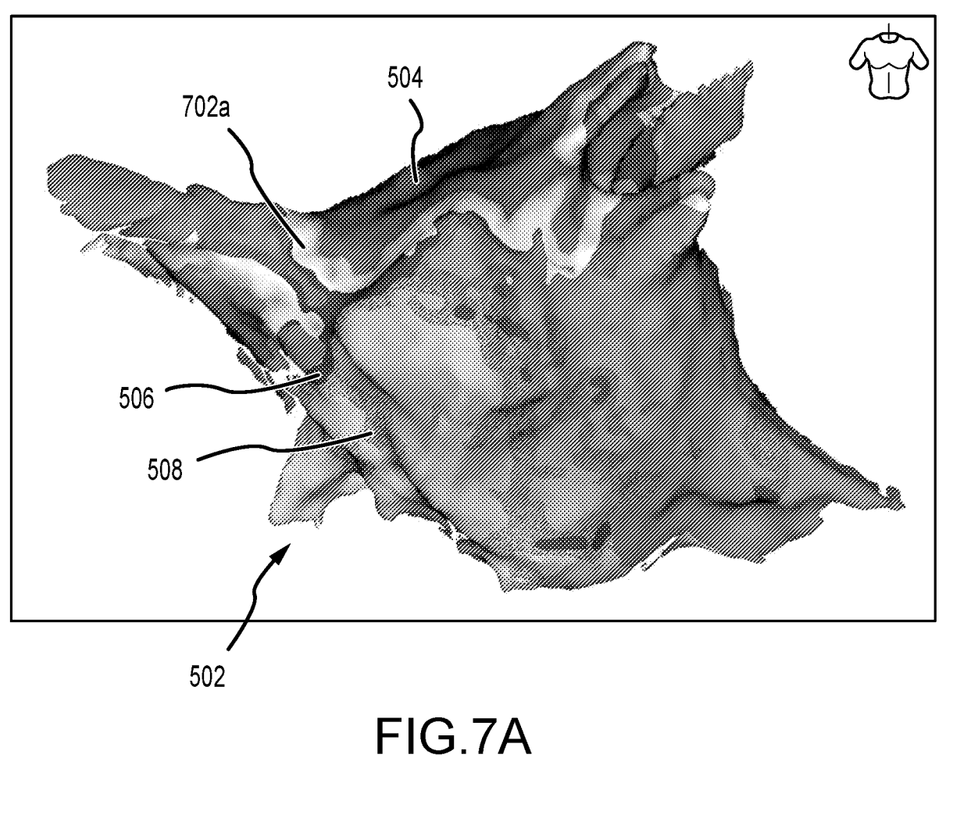
FIGS. 7A-7C depict the propagation of a cardiac activation wavefront on a graphical representation of a slow conduction map according to further aspects of the instant disclosure.
Figure 7B:
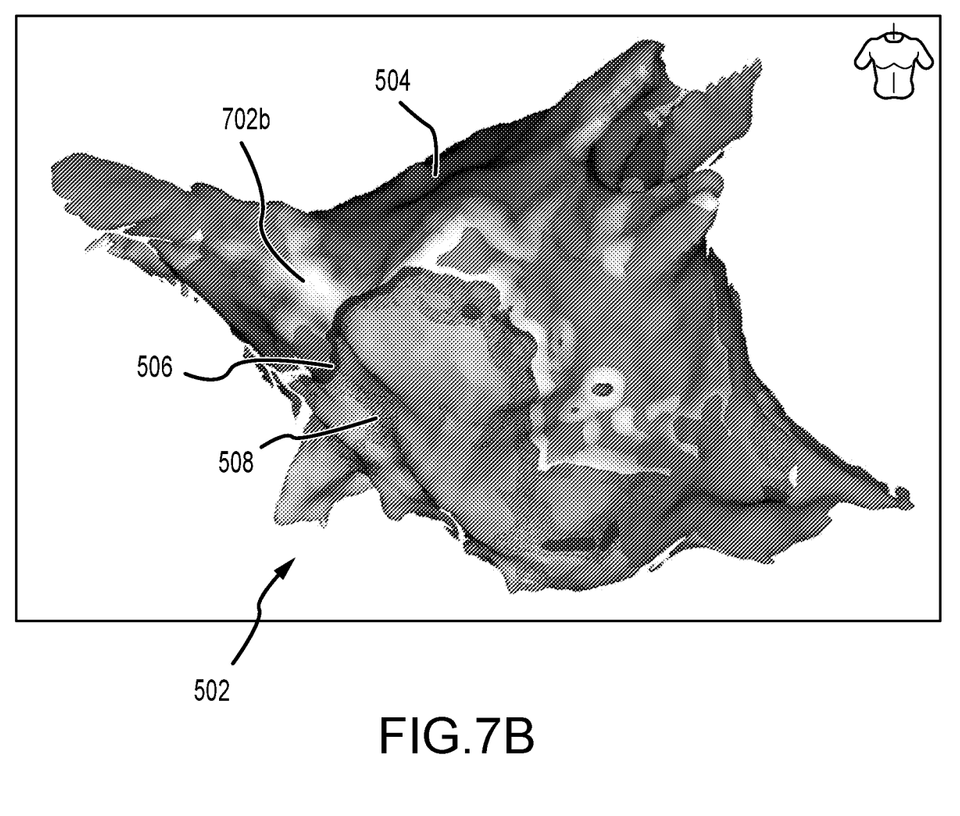
Figure 7C:
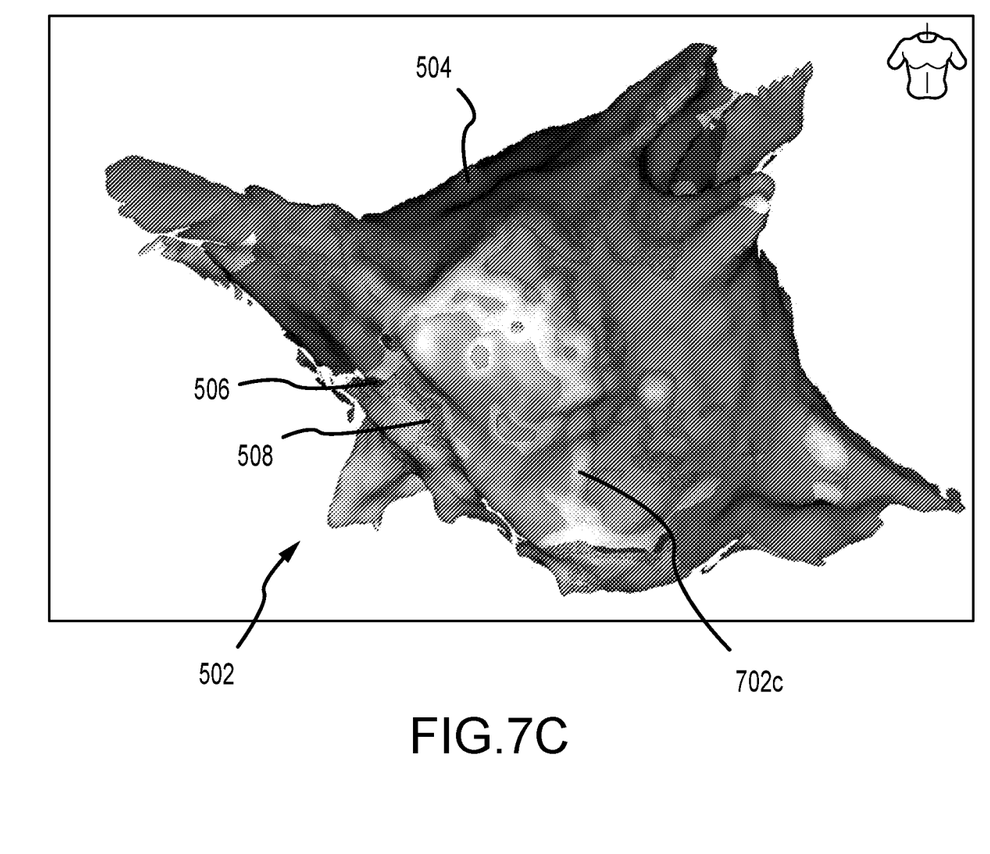

FIGS. 7A-7C depict three frames of an animated representation of a slow conduction map, added to representation 502 of FIG. 5. (FIGS. 7A-7C are in chronological sequence, though they are not immediately sequential frames.) In each frame, the position of the activation wavefront is represented by marker 702 (e.g., 702a in FIG. 7A, 702b in FIG. 7B, and 702c in FIG. 7C). Areas where marker 702 appears skinnier are areas of generally normal conduction, while areas where marker 702 appears fatter are areas of slow conduction and/or no conduction.

Although several embodiments have been described above with a certain degree of particularity, those skilled in the art could make numerous alterations to the disclosed embodiments without departing from the spirit or scope of this invention.

For example, the teachings herein can be applied in real time (e.g., during an electrophysiology study) or during post-processing (e.g., to electrophysiology data points collected during an electrophysiology study performed at an earlier time).

As another example, the slow conduction maps disclosed herein can be displayed not just as standalone maps, but also in conjunction with other electrophysiology maps (e.g., superimposed upon peak-to-peak voltage maps, complex fractionated electrogram maps, LAT maps, and the like).

As yet another example, the teachings herein can be applied not only to electrophysiology data points (e.g., as measured by electrodes 17 on catheter 13), but also to LAT values assigned (e.g., via interpolation) to individual pixels within a graphical representation (e.g., on display 23).

As a further example, the animated representation of an activation wavefront can disappear, rather than simply slowing down, in areas of no conduction.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping electrical activation of tissue, comprising:
    receiving, at an electroanatomical mapping system, a plurality of electrophysiology data points, each of the plurality of electrophysiology data points including local activation timing information; and
    for each of the plurality of electrophysiology data points, the electroanatomical mapping system computing a slow conduction metric from the local activation timing information,
    wherein the electroanatomical mapping system computing the slow conduction metric from the local activation timing information comprises the electroanatomical mapping system computing the slow conduction metric using at least one of a weighted variance of the local activation timing information and a weighted standard deviation of the local activation timing information, where weighting is inversely related to distance from the respective electrophysiology data point,
    thereby creating a slow conduction map.

2. The method according to claim 1, further comprising:
    the electroanatomical mapping system classifying a first subset of the plurality of electrophysiology data points as no conduction electrophysiology data points; and
    the electroanatomical mapping system classifying a second subset of the plurality of electrophysiology data points as slow conduction electrophysiology data points.

3. The method according to claim 1, further comprising the electroanatomical mapping system outputting a graphical representation of the slow conduction map on a three-dimensional anatomical surface model.

4. The method according to claim 3, wherein the electroanatomical mapping system outputting a graphical representation of the slow conduction map on a three-dimensional anatomical surface model comprises:
    the electroanatomical mapping system graphically representing regions of no conduction on the three-dimensional anatomical surface model using a first display convention; and
    the electroanatomical mapping system graphically representing regions of slow conduction on the three-dimensional anatomical surface model using a second display convention.

5. The method according to claim 3, wherein the graphical representation of the slow conduction map comprises an animated representation of an activation wavefront propagating along the three-dimensional anatomical surface model.

6. The method according to claim 5, wherein the electroanatomical mapping system generates the animated representation of the activation wavefront propagating along the three-dimensional anatomical surface model by executing steps comprising:
    generating a series of frames, wherein each frame of the series of frames corresponds to an image of the slow conduction map at a point in time and includes a static representation of the activation wavefront at the point in time, wherein a visibility of the static representation of the activation wavefront at the point in time is related to the slow conduction metric at a position of the activation wavefront at the point in time; and
    the electroanatomical mapping system displaying the series of frames in chronological sequence.

7. The method according to claim 6, wherein the visibility of the static representation of the activation wavefront is directly related to the slow conduction metric at the position of the activation wavefront at the point in time.

8. A method of mapping electrical activation of tissue, comprising:
    receiving a local activation time map comprising a plurality of electrophysiology data points, each electrophysiology data point including local activation timing information; and
    for each electrophysiology data point of the plurality of electrophysiology data points, computing a slow conduction metric using the local activation timing information for a subset of the plurality of electrophysiology data points within a preset distance of the respective electrophysiology data point,
    wherein the slow conduction metric is computed using one of a weighted variance of the local activation timing information for the subset of the plurality of electrophysiology data points and a weighted standard deviation of the local activation timing information for the subset of the plurality of electrophysiology data points,
    thereby creating a slow conduction map.

9. The method according to claim 8, where weighting is inversely related to distance from the respective electrophysiology data point.

10. The method according to claim 8, further comprising outputting a graphical representation of the slow conduction map on a three-dimensional anatomical surface model.

11. The method according to claim 10, wherein the graphical representation of the slow conduction map comprises:
    a graphical representation of at least one region of no conduction represented on the three-dimensional anatomical surface model using a first display convention; and
    a graphical representation of at least one region of slow conduction represented on the three-dimensional anatomical surface model using a second display convention.

12. The method according to claim 10, wherein the graphical representation of the slow conduction map comprises an animated representation of a cardiac activation wavefront.

13. The method according to claim 12, wherein the animated representation of the cardiac activation wavefront comprises a plurality of frames, wherein each frame includes a static representation of the cardiac activation wavefront at a playback time, and wherein a visibility of the static representation of the cardiac activation wavefront is related to the slow conduction metric at a position of the cardiac activation wavefront at the playback time.

14. The method according to claim 13, wherein the visibility of the static representation of the cardiac activation wavefront is directly related to the slow conduction metric at the position of the cardiac activation wavefront at the playback time.

15. An electroanatomical mapping system for generating a map of electrical activation of tissue, comprising:
   an activation mapping processor configured to:
      receive a local activation time map comprising a plurality of electrophysiology data points, each electrophysiology data point including local activation timing information; and
      for each electrophysiology data point of the plurality of electrophysiology data points, compute a slow conduction metric using the local activation timing information for a subset of the plurality of electrophysiology data points within a preset distance of the respective electrophysiology data point,
   wherein the slow conduction metric is computed using one of a weighted variance of the local activation timing information for the subset of the plurality of electrophysiology data points and a weighted standard deviation of the local activation timing information for the subset of the plurality of electrophysiology data points,
   thereby creating a slow conduction map.

16. The system according to claim 15, further comprising a mapping processor configured to output a graphical representation of the slow conduction map.

17. The system according to claim 16, wherein the graphical representation of the slow conduction map comprises an animated representation of a cardiac activation wavefront.

* * * * *